(12) United States Patent
Romano et al.

(10) Patent No.: US 6,204,024 B1
(45) Date of Patent: Mar. 20, 2001

(54) CCR5 RNA TRANSCRIPTION BASED AMPLIFICATION ASSAY

(75) Inventors: Joseph W. Romano, Derwood; Eun Mi Lee, Laurel, both of MD (US)

(73) Assignee: Akzo Nobel N.V., Arnhem (NL)

( * ) Notice: Subject to any disclaimer, the term of this patent is extended or adjusted under 35 U.S.C. 154(b) by 0 days.

(21) Appl. No.: 08/928,465

(22) Filed: Sep. 12, 1997

(51) Int. Cl.[7] ............... C12Q 1/68; C12P 19/34; C07H 21/04; C07H 21/00

(52) U.S. Cl. ............... 435/91.1; 435/6; 435/91.2; 536/24.3; 536/24.32; 536/24.33; 536/25.32

(58) Field of Search ............... 435/91.2, 91.1, 435/6; 536/24.3, 24.32, 24.33, 25.32

(56) References Cited

U.S. PATENT DOCUMENTS

| | | | |
|---|---|---|---|
| 5,234,809 | 8/1993 | Boom et al. | 435/91 |
| 5,346,686 | 9/1994 | Lyle et al. | 424/1.41 |
| 5,409,818 | 4/1995 | Davey et al. | 435/91.21 |
| 5,413,778 | 5/1995 | Kunkel et al. | 424/1.41 |
| 5,532,151 | 7/1996 | Chantry et al. | 435/184 |
| 5,554,517 | 9/1996 | Davey et al. | 435/91.21 |
| 5,591,618 | 1/1997 | Chantry et al. | 435/194 |
| 5,602,008 | 2/1997 | Wilde et al. | 435/695 |
| 5,605,671 | 2/1997 | Lyle et al. | 424/1.41 |
| 5,688,927 | 11/1997 | Godiska et al. | 530/388.23 |
| 5,705,360 | 1/1998 | Rollins et al. | 435/69.1 |
| 5,707,815 | 1/1998 | Charo et al. | 435/7.2 |
| 5,824,507 | * 10/1999 | Kim et al. | 435/69.3 |
| 5,888,819 | * 3/1999 | Goelet et al. | 435/6 |
| 6,057,102 | * 5/2000 | Landau et al. | 435/6 |

FOREIGN PATENT DOCUMENTS

| | | |
|---|---|---|
| WO 94/11504 | 5/1994 | (WO) . |
| WO 95/35376 | 12/1995 | (WO) . |
| WO 9712914-A1 | 2/1996 | (WO) . |
| WO 96/22371 | 7/1996 | (WO) . |
| WO 96/23068 | 8/1996 | (WO) . |
| WO 96/38559 | 12/1996 | (WO) . |
| WO 96/39434 | 12/1996 | (WO) . |
| WO 96/39437 | 12/1996 | (WO) . |
| WO 97/00691 | 1/1997 | (WO) . |
| WO 97/00893 | 1/1997 | (WO) . |
| WO 9722698 | 6/1997 | (WO) . |
| WO 9732019 | 9/1997 | (WO) . |
| WO 9805798 | 2/1998 | (WO) . |

OTHER PUBLICATIONS

Cocchi et al., *Nature Medicine*, 2 (11):1244–1247 (Nov. 1996).
Samson et al., *Biochemistry*, 35 (11):3361–3367, (1996).
Huang et al., *Nature Medicine*, 2 (11):1240–1243 (Nov. 1996).
Lui et al., *Cell*, 86:367–377 (Aug. 1996).
Samson et al., *Nature*, 382:722–725 (Aug. 22, 1996).
Premack et al., *Nature Medicine*, 2 (11):1174–1178 (Nov. 1996).
D'Souza et al., *Nature Medicine*, 2 (12):1293–1300 (Dec. 1996).
Dragic et al., *Nature*, 381:667–673 (1996).
Wu et al, *Journal of Experimental Medicine*, 185:9:1681–1691, May 5, 1997.
Raport et al., *The Journal of Biological Chemistry*, 271:29:17161–17166, 1996.
van Gemen et al., *Journal of Virological Methods*, 49:157–167, Jan. 1, 1994.
Zimmerman et al., *Molecular Medicine*, 3:1:23–26, 1997.
Romano et al., *Clinics in Laboratory Medicine*, 16:1:89–103, Mar. 1, 1996.

\* cited by examiner

*Primary Examiner*—W. Gary Jones
*Assistant Examiner*—Joyce Tung
(74) *Attorney, Agent, or Firm*—Mary E. Gormley; Michael G. Sullivan

(57) ABSTRACT

A method and a test kit for genotyping the CCR5 chemokine receptor. CCR5 transcript DNA is amplified using transcription based amplification. The amplification product is detected through the hybridization of appropriately labeled oligonucleotide wild type and mutant probes. In a liquid hybridization based ECL analysis, the mutant probe is a 16mer having the sequence 5'TCCATACATTAAAGAT3' [SEQ ID NO:9]. The method and kit can be used to predict.

18 Claims, 2 Drawing Sheets

SEQUENCE LISTING (1) GENERAL INFORMATION:

(iii) NUMBER OF SEQUENCES: 10

(2) INFORMATION FOR SEQ ID NO:1:

(i) SEQUENCE CHARACTERISTICS:
      (A) LENGTH: 47 base pairs
      (B) TYPE: nucleic acid
      (C) STRANDEDNESS: single
      (D) TOPOLOGY: Not Relevant (ii) MOLECULE TYPE: other nucleic acid
      (A) DESCRIPTION: /desc = "DNA Oligonucleotide"

(iii) HYPOTHETICAL: NO (ix) FEATURE:
      (A) NAME/KEY: misc_feature
      (B) LOCATION: 1..25
      (D) OTHER INFORMATION: /label= T7 RNA Polymere (xi) SEQUENCE DESCRIPTION: SEQ ID NO:1:

AATTCTAATA CGACTCACTA TAGGGAGCAG CGGCAGGACC AGCCCCA      47

(2) INFORMATION FOR SEQ ID NO:2:

(i) SEQUENCE CHARACTERISTICS:
        (A) LENGTH: 54 base pairs
        (B) TYPE: nucleic acid
        (C) STRANDEDNESS: single
        (D) TOPOLOGY: Not Relevant (ii) MOLECULE TYPE: other nucleic acid
        (A) DESCRIPTION: /desc = "DNA Oligonucleotide"

(iii) HYPOTHETICAL: NO (ix) FEATURE:
        (A) NAME/KEY: misc_feature
        (B) LOCATION: 1..25
        (D) OTHER INFORMATION: /label= T7 RNA Polymera (xi) SEQUENCE DESCRIPTION: SEQ ID NO:2:

AATTCTAATA CGACTCACTA TAGGGAGAGA TTCCCGAGTA GCAGATGACC ATGA         54

(2) INFORMATION FOR SEQ ID NO:3:

(i) SEQUENCE CHARACTERISTICS:
        (A) LENGTH: 22 base pairs
        (B) TYPE: nucleic acid
        (C) STRANDEDNESS: single
        (D) TOPOLOGY: Not Relevant (ii) MOLECULE TYPE: other nucleic acid
        (A) DESCRIPTION: /desc = "DNA Oligonucleotide"

(iii) HYPOTHETICAL: NO (xi) SEQUENCE DESCRIPTION: SEQ ID NO:3:

GGCTGTGTTT GCGTCTCTCC CA                                           22

(2) INFORMATION FOR SEQ ID NO:4:

(i) SEQUENCE CHARACTERISTICS:
        (A) LENGTH: 22 base pairs
        (B) TYPE: nucleic acid
        (C) STRANDEDNESS: single
        (D) TOPOLOGY: Not Relevant (ii) MOLECULE TYPE: other nucleic acid
        (A) DESCRIPTION: /desc = "DNA Oligonucleotide"

(iii) HYPOTHETICAL: NO (xi) SEQUENCE DESCRIPTION: SEQ ID NO:4:

AGCAGCGGCA GGACCAGCCC CA                                           22

(2) INFORMATION FOR SEQ ID NO:5:

(i) SEQUENCE CHARACTERISTICS:
        (A) LENGTH: 29 base pairs
        (B) TYPE: nucleic acid
        (C) STRANDEDNESS: single
        (D) TOPOLOGY: Not Relevant (ii) MOLECULE TYPE: other nucleic acid
        (A) DESCRIPTION: /desc = "DNA Oligonucleotide"

(iii) HYPOTHETICAL: NO (xi) SEQUENCE DESCRIPTION: SEQ ID NO:5:

AGAGATTCCC GAGTAGCAGA TGACCATGA                                    29

```
(2) INFORMATION FOR SEQ ID NO:6:

(i) SEQUENCE CHARACTERISTICS:
        (A) LENGTH: 25 base pairs
        (B) TYPE: nucleic acid
        (C) STRANDEDNESS: single
        (D) TOPOLOGY: Not Relevant (ii) MOLECULE TYPE: other nucleic acid
        (A) DESCRIPTION: /desc = "DNA Oligonucleotide"

(iii) HYPOTHETICAL: NO (xi) SEQUENCE DESCRIPTION: SEQ ID NO:6:

TTTGGGGTGG TGACAAGTGT GATCA                                              25

(2) INFORMATION FOR SEQ ID NO:7:

(i) SEQUENCE CHARACTERISTICS:
        (A) LENGTH: 25 base pairs
        (B) TYPE: nucleic acid
        (C) STRANDEDNESS: single
        (D) TOPOLOGY: Not Relevant (ii) MOLECULE TYPE: other nucleic acid
        (A) DESCRIPTION: /desc = "DNA Oligonucleotide"

(iii) HYPOTHETICAL: NO (xi) SEQUENCE DESCRIPTION: SEQ ID NO:7:

AGTATCAATT CTGGAAGAAT TTCCA                                              25

(2) INFORMATION FOR SEQ ID NO:8:

(i) SEQUENCE CHARACTERISTICS:
        (A) LENGTH: 28 base pairs
        (B) TYPE: nucleic acid
        (C) STRANDEDNESS: single
        (D) TOPOLOGY: Not Relevant (ii) MOLECULE TYPE: other nucleic acid
        (A) DESCRIPTION: /desc = "DNA Oligonucleotide"

(iii) HYPOTHETICAL: NO (xi) SEQUENCE DESCRIPTION: SEQ ID NO:8:

TCATTTTCCA TACATTAAAG ATAGTCAT                                           28

(2) INFORMATION FOR SEQ ID NO:9:

(i) SEQUENCE CHARACTERISTICS:
        (A) LENGTH: 16 base pairs
        (B) TYPE: nucleic acid
        (C) STRANDEDNESS: single
        (D) TOPOLOGY: Not Relevant (ii) MOLECULE TYPE: other nucleic acid
        (A) DESCRIPTION: /desc = "DNA Oligonulceotide"

(iii) HYPOTHETICAL: NO (xi) SEQUENCE DESCRIPTION: SEQ ID NO:9:

TCCATACATT AAAGAT                                                        16

(2) INFORMATION FOR SEQ ID NO:10:

(i) SEQUENCE CHARACTERISTICS:
        (A) LENGTH: 27 base pairs
        (B) TYPE: nucleic acid
        (C) STRANDEDNESS: single
        (D) TOPOLOGY: Not Relevant
```

-continued

```
    (ii) MOLECULE TYPE: other nucleic acid
         (A) DESCRIPTION: /desc = "DNA Oligonucleotide"

(iii) HYPOTHETICAL: NO (xi) SEQUENCE DESCRIPTION: SEQ ID NO:10:

AAAGAAGGTC TTCATTACAC CTGCAGC                                              27
```

CCR5 RNA TRANSCRIPTION BASED AMPLIFICATION ASSAY

FIELD OF THE INVENTION

The present invention is directed to a method and kit for genotyping the CCR5 chemokine receptor by amplifying the CCR5 RNA transcript using transcription based amplification. The present invention is also directed to oligonucleotides for amplifying the CCR5 RNA transcript and to mutant and wild type specific probes used in the detection of the amplification product.

BACKGROUND OF THE INVENTION

The CCR5 chemokine receptor is known to act as a coreceptor in conjunction with CD4 for the entry of macrophage tropic nonsyncytia-inducing (NSI) strains of HIV-1 during infection. The NSI, or macrophage tropic, strains are apparently the most prevalent strains in HIV positive individuals. Recent studies have indicated that the CCR5 genotype is important in predicting host susceptibility to HIV-1 infection as well as determining disease progression.

A 32 base deletion mutation in the CCR5 gene has been found to occur in some individuals. Individuals who are homozygous for this deletion mutation do not express the CCR5 receptor on the surface of their CD4+ cells and appear not to be injectable by NSI isolates of HIV-1. Individuals who are heterozygous for this deletion mutation, i.e., have a wild type (wt) CCR5 allele and a mutant (mut) CCR5 allele, appear to be injectable, but disease progression is less rapid and less severe than that of individuals who are homozygous for the wild type allele.

In view of the apparent relationship of the CCR5 genotype to HIV-1 infection and progression, an assay method that can determine whether an individual is homozygous mutant, heterozygous, or homozygous wild type at the CCR5 gene can serve as a diagnostic marker for (1) infectability by NSI forms of HIV-1 and (2) disease progression prognoss.

SUMMARY OF THE INVENTION

According to the present invention a method for genotyping the CCR5 chemokine receptor has been discovered that utilizes transcription based amplification, such as the isothermal transcription based amplification commonly known as NASBA (nucleic acid sequence based amplification). In the assay method of the invention, CCR5 transcript RNA is amplified according to a transcription based amplification procedure that uses a pair of oligonucleotides to target and amplify both the wild type and the mutant type transcript RNA's. The amplificate is captured or immobilized and the alleles are detected by means of independent hybridizations using wild type and mutant specific probes.

DETAILED DESCRIPTION

Figure 1A:
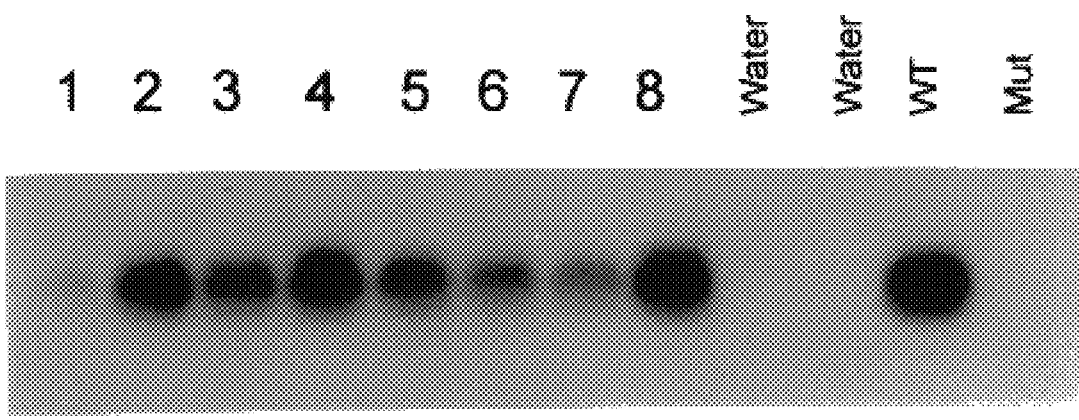
FIG. 1 shows results of an assay of patient samples using a blot based hybridization system.

Any transcription based amplification method that amplifies the CCR5 RNA transcript can be used in the assay method according to the present invention for genotyping the CCR5 chemokine receptor.

Transcription based amplification techniques usually comprise treating target nucleic acid with two oligonucleotides, one of which comprises a promoter sequence, to generate a template that includes a functional promoter. Known and useful promoters are those that are recognized by certain bacteriophage RNA polymerases, such as T3, SP6 and T7. Multiple copies of RNA are transcribed from said template and can serve as a basis for further amplification.

The preferred amplification method of the present invention is the isothermal transcription based amplification system referred to as NASBA. The NASBA methodology is disclosed in U.S. Pat. Nos. 5,409,818 and 5,554,527, which are incorporated herein by reference. The NASBA amplification system amplifies RNA. This is advantageous for the genotyping of the CCR5 chemokine receptor gene because the RNA transcripts for this gene are expressed at a copy number that is significantly higher than the two copies per cell for the CCR5 gene at the DNA level. Another advantage is that NASBA is performed at a relatively constant ambient temperature, which ensures that the enzymes used in the process do not lose their activity. Also, the assay method of the present invention using the NASBA system can be applied to cellular extracts or to fixed preparations in situ and there is no concern regarding a DNA background.

The fact that genotyping of the CCR5 gene could be determined using an RNA amplification system such as NASBA could not be reasonably predicted because, first, for RNA to be useful for the genotyping, both alleles (maternal and paternal) must be transcribed. Because of the possibility of allelic exclusion, i.e., no transcription of one allele, it was not known whether both alleles would be transcribed. Also, both alleles must be expressed at sufficiently high levels to be typed by the assay. Whether both alleles of the CCR5 gene would be transcribed into RNA at sufficient levels to be typed by an assay was not known.

Amplification in the NASBA system is achieved generally through the coordinated activities of three enzymes (reverse transcriptase, RNase H, and RNA polymerase) and two DNA oligonucleotides (referred to herein as primers) specific for the target sequence of interest. Preferably, the reverse transcriptase is avian myeloblastosis virus reverse transcriptase and the RNA polymerase is T7 RNA polymerase. By attaching a T7 RNA polymerase promoter to the first oligonucleotide (P1), a double stranded promoter is generated through the action of RNase H and AMV-reverse transcriptase. Through the subsequent action of T7 RNA polymerase, large amounts of anti sense RNA corresponding to the original target are produced. This material can then serve as template in a subsequent amplification phase of the process. The reaction produces large amounts of single stranded RNA which is antisense to the original target sequence. The single stranded RNA product can be readily detected through the hybridization of an appropriately labeled oligonucleotide DNA probe.

In the assay method of the present invention a single pair (or set) of oligonucleotides is used to amplify both the mutant and wild type alleles. Two sets of oligonucleotides, specific for the CCR5 amplification, were prepared by a commercial source (Operon, Inc.). Design of these oligonucleotides was based on the reported sequence for the CCR5 gene (GenBank Accession Number: U57840). The nucleotides used in the assay span different positions located between bases 430 and 650 of the CCR5 gene. There are two antisense P1 sequences downstream from the 32 base deletion mutation site (positions 554 to 585) and two sense P2 sequences upstream from this region. The map positions are: P1A=602 to 623, P1B=626 to 650, P2A=465 to 486 and P2B=430 to 454, where numbering is based on the A of ATG (methionine) being base No. 1. The sequences of the oligonucleotides are as follows:
P 1 A=5'AATTCTAATACGACTCACTATAGGGAGCAGCG GCAGGACCAGCCCCA3';[SEQ ID NO:1]
P 1 B=5'AATTCTAATACGACTCACTATAGGGAGAGATT CCCGAGTAGCAGATGA CCATGA3';[SEQ ID NO: 2]
P2A=5'GGCTGTGTTTGCGTCTCTCCCA3'[SEQ ID NO: 3]; and
P2B=5'TTTGGGGTGGTGACAAGTGTGATCA3'[SEQ ID NO: 6].

The italicized sequences of the P1 oligonucleotides (A and B) designate the overhang portion encoding the T7 RNA polymerase promoter. This portion of the oligonucleotide can be replaced by another suitable promoter sequence when using another RNA polymerase in the amplification.

The combination of the P1A and P2B primers produces the maximum amount of NASBA product as determined by visual evaluation of autoradiograms. P1A/P2A, P1B/P2B and P1B/P2A primer pairs also give good results but not as good as the P1A/P2B pair.

The method according to the present invention can be practiced on fixed preparations for in situ analysis. According to this embodiment of the method, cells are fixed and then permeabilized to optimize permeability of the cell membranes. The fixatives are those standardly used in the art for cell or tissue preprations, such as acetone and methanol, ethanol, formalin, formaldehyde, paraform ldehyde, or Permafix©, and the permeabilization is done by proteinases, such as proteinase K or pepsinogen. The cells are then washed to remove all reagents which might inhibit the amplification reaction. Permeabilization is done to the point that the cells allow entry of all necessary amplification reaction components, yet retain the targets and amplification products within the cells. Detection of amplificates may be by in situ hybridization with an appropriately labeled probe.

The assay according to the present invention using isothermal NASBA amplification is preferably applied in vitro to either whole blood or peripheral blood mononuclear cells (PBMC). The PBMC can be obtained from whole blood either by centrifugation through Ficoll Hypaque or through the use of cell preparation tubes. The RNA is obtained by applying extraction methodology such as that disclosed in Boom et al, U.S. Pat. No. 5,234,809, to the whole blood or the PBMC blood cells. The disclosure of U.S. Pat. No. 5,234,809 is incorporated herein by reference.

The NASBA amplification of the CCR5 transcript RNA is carried out under conditions that can be readily determined by a person of ordinary skill in the art, particularly, by reference to the above cited patents. In a preferred procedure according to the present invention, amplification was achieved in a 20 µL reaction containing 5 µL of the nucleic acid extract material in 40 mM Tris, pH 8.5, 5 mM dithiothritol, 12 mM MgCl$_2$, 70 mM KCl, 2.0 mM each of ATP, CTP, UTP, 1.5 mM GTP, 0.5 mM ITP, 1.0 mM each of dATP, dCTP, dGTP, dTTP, 1.5 M sorbitol, 2.1 µg BSA, 0.08 unit RNase H, 32 units T7 RNA polymerase, 6.4 units of AMV-RT, 15% DMSO and 0.2 µM of each oligonucleotide, e.g., P1A and P2B.

Detection of the CCR5 NASBA amplification product is achieved through the hybridization of an appropriately labeled oligonucleotide DNA probe. Various labeling moieties are known in the art and may, for example, be a radioactive compound, a detectable enzyme (such as HRP), or any other moiety capable of generating a detectable signal, such as calorimetric, fluorescent, chemiluminescent or electochemiluminescent signal. Discriminating between the two amplification products is achieved in the detection step by means of independent hybridizations with a mutant and wild type probe, respectively. Both blot based hybridization analysis and liquid hybridization based ECL (electrochemiluminescence) analysis are preferably used, although other analysis systems such as ELGA (enzymelinked gel analysis) and in situ hybridization will also work.

In a blot based hybridization analysis the wild type and mutant probes are each hybridized in a standard procedure to Southern transfer blots or vacuum transferred blots containing the NASBA amplificates. The portion of the CCR5 gene targeted by the P1 and P2 primers in the NASBA amplification spans positions 430 through 650. A probe useful for the wild type amplification product anneals to the position corresponding to bases 557–581 of the CCR5 wild type allele amplification product and has the sequence 5'AGTATCAATTCTGGAAGAATTTCCA3 [SEQ ID NO:7]. The position corresponding to bases 557–581 is within the portion of the gene deleted in the mutant allele. A probe specific for the mutant allele corresponds to base positions 540–553 and 586–599 of the wild type allele, which are a continuous sequence in the deletion mutation allele. The mutant probe has the sequence 5'TCATTTTCCATACATTAAAGATAGTCAT3'[SEQ ID NO:8]. This probe will hybridize to the mutant form of the gene where base 553 is immedi tely adjacent to base 586 because of the deletion.

In a typical blot based hybridization analysis of the CCR5 NASBA amplification products, the products are transferred to nylon membranes by vacuum using 2×SSC buffer using either a slot blot apparatus or, by vacuum transfer after electrophoretic resolution through agarose gels. After transfer, the blots are hybridized with probes that are 5'-end labeled with $^{32}$p using standard methods. After hybridization (16–20 hours), the blots are washed 3 to 4 times with 1×SSC, 1% SDS at 50° C.

Figure 2:
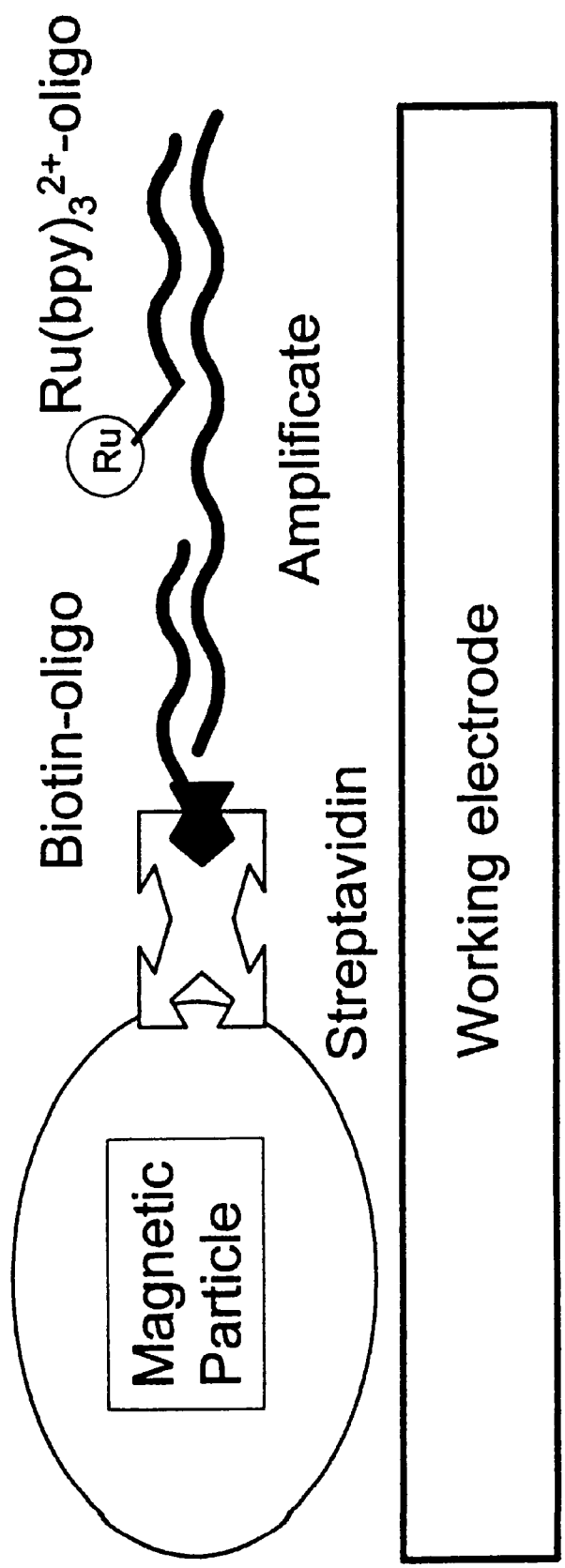
FIG. 2 is a schematic diagram illustrating detection of an amplification product according to the present invention.

In a liquid hybridization based ECL analysis, detection of an allele is achieved through a single hybridization reaction involving: (1) a biotinylated capture probe immobilized onto the surface of a streptavidin coated magnetic bead, and (2) a ruthenium labeled detector probe which is responsible for the actual ECL reaction (refer to FIG. 2).

The hybridization product is loaded into an ECL reader (e.g., the NASBA QR System) and the amount of light produced is determined by a photomultipliertube (PMT). The amount of light produced by the ECL process is a function of the amount of amplification product that is generated. Since the product of the amplification process is single stranded RNA, the product can be detected by hybridization directly without the need for a denaturing step.

The capture probe used in the liquid hybridization based ECL analysis hybridizes to an area which is common to both the mutant and wild type alleles in the amplification product. A capture probe useful in the liquid hybridization based ECL analysis of the CCR5 NASBA amplification product has the sequence:
bio-5'AAAGAAGGTCTTCATTACACCTGCAGC3' [SEQ ID NO:10].

The map positions are 511–537.

The wild type probe useful in the blot based hybridization analysis can also be used in liquid hybridization based ECL analysis. The mutant probe useful in the blot based hybridization analysis, however, cannot be used in a liquid hybridization based ECL assay. The 28 mer mutant probe cross hybridizes to wild type NASBA product in liquid hybridization. This cross reactivity is believed to be relative to the existence of a duplication in the wild type sequence. With the exception of two mismatch bases, the 12 bases that occur in the wild type CCR5 gene immediately upstream of the region deleted in the mutant gene are duplicated as the last 12 bases of the 32 bases deleted in the mutant gene.

It has been discovered according to the present invention that a 16 base mutant probe having the sequence 5'TCCATACATTAAAGAT3'[SEQ ID NO:9] and consisting of the 8 bases immediately upstream of the deletion and the 8 bases immediately downstream of the deletion does not cross hybridize to the wild type RNA NASBA products in the liquid hybridization based ECL reaction. The fact that the 16mer mutant robe is specific for the mutant target is somewhat surprising because it has only one mismatch (five bases in from the 5' end) relative to the wild type target. The 28 mer mutant probe has a total of four mismatches; two at the 5' end, one at four bases in from the 5' end and one eleven bases in from the 5' end. Although the 28mer has more mismatches relative to the 16 mer, only the 28mer cross hybridizes to wild type product in liquid hybridization. The shorter length of the 16mer is apparently responsible for its specificity although the precise reason therefor is not clear. It is assumed that the particular positions of the mismatches are contributing factors for the specificity.

The assay according to the present invention is of approximately equal sensitivity for both forms of the CCR5 RNA and is able to detect between 5 and 50 copies of RNA in the NASBA system. The assay has an extremely high sensitivity with $5\times10^3$ copies of wild type RNA being detectable in a background of $5\times10^5$ copies of mutant RNA. Alternatively, $5\times10^2$ copies of mutant RNA can be detected in a background of $5\times10^5$ wild type RNA molecules.

Test kits for the genotyping of the CCR5 receptor in clinical samples are also part of the present invention. A test kit according to the invention may comprise a pair of oligonucleotides (selected from the P1 and P2 oligonucleotides) for the amplification and a wild type and a mutant probe. In a preferred embodiment, the test kit comprises the oligonucleotides
P1A: 5'AATTCTAATACGACTCACTATAGGGAG-CAGCGGC
AGACCAGCCCCA3'[SEQ ID NO:1], (where the italicized sequence designates the T7 RNA polymerase promoter) and
P2B: 5'TTTGGGGTGGTGACAAGTGTGATCA3'[SEQ ID NO:2], for the amplification,
5'AGTATCAATTCTGGAAGAATTTCCA3'[SEQ ID NO:7], as the wild-type probe, and one of 5'TCATTTTCCATACATTAAAGATAGTCAT3'[SEQ ID NO:5] and 5'TCCATACATTAAAGAT3' [SEQ ID NO:9] as the mutant probe, both probes labelled at the 5' end with a detectable label. A kit for use in an ECL based hybridization preferably comprises, in addition to the P1A nd P2B amplification oligonucle otides, the 5'TCCATACATTAAAGAT3' [SEQ ID NO:9] oligonucleotide as the mutant probe and the capture probe bio-5'AAAGAAGGTCTTCATTACACCTGCAGC3'[SEQ ID NO:9]. Such kits may also comprise suitable amplification reagents such as RNase H, reverse transcriptase and RNA polymerase.

EXAMPLE 1

CCR-5 In vitro RNA sensitivity and specificity by $^{32}$p Detection

Dilutions of control RNA transcripts produced in vitro (in vitro RNA) were used to evaluate the sensitivity and speci-ficity of the CCR-5 NASBA assay Clones for both wild type and mutant alleles were used to produce the respective RNA by use of Riboprobe System-T7 in vitro transcription kit (Promega, Inc.). DNase treatment was done on the resulting transcription products and then the RNeasy Mini Kit (Qiagen) protocol was followed. O.D. 260 absorbance was measured and used to calculate RNA copy number. Appropriate dilutions were made and NASBA was done on ten-fold dilutions of wild type and mutant RNA controls starting with $5\times10^3$ copies down to $5\times10^{-1}$ copies. To the RNA dilutions, 10 µl primer premix (5X NN buffer, DMSO, 2 amplification oligonucleotides, water) was added and the mixture was incubated at 65° C. for 5 minutes. The mixture was cooled to 41° C. for 5 minutes. Then, 5 µl of enzyme mix (BSA, sorbitol, RNase H, T7 RNA polymerase, AMV-RT) was added. The final concentration of the ingredients is as given in the preferred procedure described above. The mixture was then left on a heat block with gentle shaking for 90 minutes. The NASBA amplification products were transferred in duplicate to nylon membranes by vacuum using a slot blot apparatus and 2xSSC buffer. The blots were then hybridized with both wild type and mutant probes that were 5'-end labeled with $^{32}$p. The mutant probe used in this detection was the 28mer. Hybridization was done overnight, 16–20 hours, and the blots were washed 3 times with 1xSSC/1%SDS at 50° C. The results were vie wed by autoradiographs. There was no crossreactivity, i.e., the probes were specific. Both types of CCR-5 RNA had approximate equal sensitivity which is between 5 and 50 copies of RNA. Two trials were done to confirm results.

EXAMPLE 2

CCR-5 In vitro RNA Sensitivity and Specificity by ECL Detection

Amplification products of CCR-5 control RNA dilutions were evaluated by ECL detection, as is generally described in van Gemen et al., J. of Virol Methods, Vol. 49, pp 157–168 (1994). The amplified product was diluted 1:20. The hybridization reaction was done by adding together $2\times10^{12}$ molecules CCR-5 biotinylated capture probe, $2\times10^{12}$ molecules CCR-5 ruthenium labeled detector probe (either wild type or the 16mer mutant probe) and the diluted amplificate. The tubes with this reaction mix were heated for 5 minutes at 60° C. and then maintained for 30 minutes at 41° C. in a shaking water bath. Subsequently, 300 µl of TPA solution (1.4% TPA in PBS and Triton X-100, pH 7.5) was added and the tubes were then analyzed by the NASBA QR System which gives a reading for the wild type probe and the 16mer mutant probe. In general, both wild type and mutant RNA have a sensitivity between 5 and 50 copies. In trial $1.5\times10^0$ copies of mutant RNA was negative but in trial 2 it was positive. This matches the $^{32}$p results which were negative in trial 1, but a low positive in trial 2. The ECL detection was also specific since wild type probe did not detect mutant in vitro RNA nd mutant probe did not detect wild type in vitro RNA.

EXAMPLE 3

Blot Based Analysis of Patient Samples

Figure 1B:
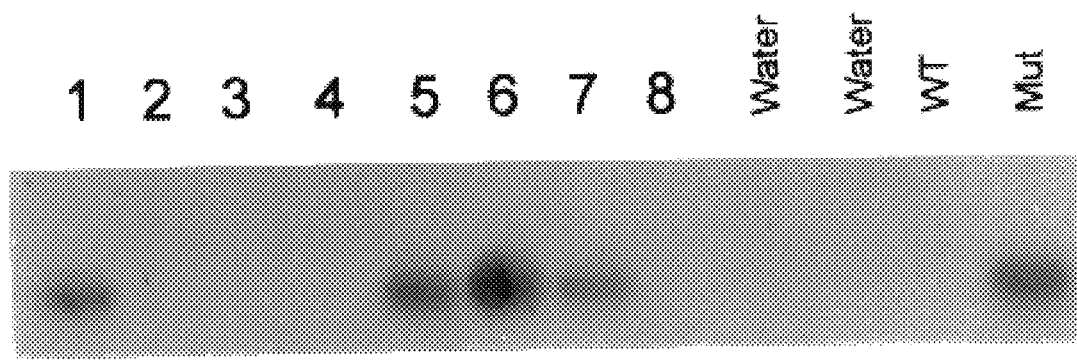

The assay method according to the present invention was applied to patient PBMC samples. Nucleic acid was isolated by the silica-based method of Eloom et at, U.S. Pat. No. 5,234,809. NASBA amplification was done with wild type and mutant controls which were $5\times10^4$ copies of in vitro RNA for each. After amplification, 5 µL of each NASBA product was resolved through an agarose gel in duplicate for detection with both probes. The gel was then vacuum transferred to a nylon membrane and hybridized overnight at 50° C. with $^{32}$p end labeled probes. The 28bp mutant probe was used. Washes were done with 1×SSC/1%SDS. The results illustrated in FIG. 1 show homozygous wild type and heterozygous patients. The probes were specific by the results of the controls.

EXAMPLE 4

Controls and Patient Samples by ECL Detection

The same amplificates from Example 3 were also detected by ECL with the ruthenium labeled wild type and ruthenium labeled 16mer mutant probes. The controls in this set included wild type and mutant assay negatives, two water controls and CCR-5 wild type and mutant in vitro RNA controls, 5×10$^4$ copies each. The results are shown in Table 1. The assay is specific and results match 100% with the $^{32}$p results.

TABLE 1

| | $^{32}$p | | ECL | |
|---|---|---|---|---|
| SAMPLE | WT | MUT | WT | MUT |
| SP1 | + | − | + | − |
| SP2 | + | − | + | − |
| SP4 | + | − | + | − |
| MK 6C | + | + | + | + |
| MK 7C | + | + | + | + |
| MK 8C | + | + | + | + |
| MK 10C | + | − | + | − |
| H1 | + | + | + | + |
| H2 | + | − | + | − |
| H3 | + | − | + | − |
| H4 | + | − | + | − |
| 2977 | + | − | + | − |
| 1270 | + | + | + | + |
| 2993 | + | − | + | − |

TABLE 1-continued

| | $^{32}$p | | ECL | |
|---|---|---|---|---|
| SAMPLE | WT | MUT | WT | MUT |
| 3042 | + | − | + | − |
| 1267 | + | − | + | − |
| 1245 | + | + | + | + |
| 1236 | + | − | + | − |
| 1237 | + | − | + | − |
| 3084 | + | − | + | − |
| 1591 | + | − | + | − |
| 1244 | + | − | + | − |
| 3027 | + | − | + | − |
| 2949 | + | − | + | − |
| 1249 | + | − | + | − |
| 2491 | + | − | + | − |

Table 2 summarizes the data obtained from application of the NASBA based assay of the present invention to multiple patient samples from various clinical groups. The data of Table 2 show that the assay can be readily applied to patient samples in order to rapidly obtain CCR5 genotype results.

TABLE 2

| PATIENTS | WT/WT | WT/MU | MU/MU |
|---|---|---|---|
| HIV-1+ | 12 | 4 | 0 |
| HIV-1 + LTS* | 2 | 1 | 0 |
| HIV-1 RISK MOTHERS | 3 | 0 | 0 |
| HTLV I | 3 | 1 | 0 |
| TOTALS | 20 | 6 | 0 |

*Long term survivor

Although the present invention has been described in conjunction with certain preferred embodiments thereof it is not to be limited thereto, but instead is intended to include all those embodiments within the scope and spirit of the a pended claims.

---

What is claimed is:

1. A method of genotyping the CCR5 chemokine receptor to determine whether an individual is homozygous mutant, heterozygous or homozygous wild type, comprising:
   (a) providing CCR5 transcript RNA of an individual to be genotyped, wherein said CCR5 transcript RNA is obtained from whole blood or peripheral blood mononuclear cells of the individual;
   (b) amplifying said CCR5 transcript RNA using an isothermal transcription based amplification method; and
   (c) determining whether an amplification product of step (b) contains a wild type CCR5 allele, a mutant CCR5 allele or both wild type and mutant CCR5 alleles by independently hybridizing amplification product with labeled wild type and mutant specific probes, and detecting the resulting hybridization products.

2. The method of claim 1 wherein said transcription based amplification is NASBA (nucleic acid based sequence based amplification).

3. The method of claim 2, wherein a pair of oligonucleotides that target positions 430 to 650 of the CCR5 gene is used in NASBA.

4. The method of claim 3, wherein one of the pair of oligonucleotides is selected from two antisense P1 sequences having map positions 602 to 623 and 620 to 650 of the CCR5 gene and the other oligonucleotide is selected from two P2 sequences having map positions 465 to 486 and 430 to 454 of the CCR5 gene.

5. The method of claim 4, wherein the P1 and P2 sequences are:
   P1A=
   5'AATTCTAATACGACTCACTATAGGGAGCAGC GGCAGGACCAGCCCCA3'[SEQ ID NO:1];
   P1B=
   5'AATTCTAATACGACTCACTATAGG-GAGAGATTCCCGAGTAGCAGATGA CCATGA3' [SEQ ID NO:2];
   P2A=5'GGCTGTGTTTGCGTCTCTCCCA3'[SEQ ID NO:3]; and
   P2B=5'TTTGGGGTGGTGACAAGTGTGATCA3'[SEQ ID NO:6], where the italicized sequence designates T7 promoter sequence.

6. The method of claim 5, wherein the pair of oligonucleotides is P1A/P2B.

7. The method of claim 1, wherein step (c) is performed using a hybridization analysis selected from blot based hybridization analysis and liquid hybridization based ECL (electrochemiluminescence) analysis.

8. The method of claim 7, wherein the hybridization analysis is blot based analysis, and wherein said wild type probe has the sequence:
   5'AGTATCAATTCTGGAAGAATTTCCA3'[SEQ ID NO:7].
   and said mutant probe has the sequence:
   5'TCATTTTCCATACATTAAAGATAGTCAT3'[SEQ ID NO:8].

9. The method of claim 7, wherein the hybridization analysis is liquid based hybridization, said wild type probe has the sequence:
   5'AGTATCAATTCTGGAAGAATTTCCA3'[SEQ ID NO:7],
   said mutant probe has the sequence:
   5'TCCATACATTAAAGAT3'[SEQ ID NO:9],
   and a capture probe has the sequence:
   5'AAAGAAGGTCTTCATTACACCTGCAGC3'[SEQ ID NO:10].

10. An oligonucleotide useful as a mutant probe in a liquid hybridization based ECL (electrochemiluminescence) assay of the nucleic acid sequence based amplification product of CCR5 transcript RNA, said oligonucleotide having the sequence:
    5'TCCATACATTAAAGAT3'[SEQ ID NO:9].

11. A method for predicting the susceptibility of an individual to infection by NSI (nonsyncytia-inducing) forms of HIV-1 (human immunodeficiency virus-1) and for predicting disease progression of an individual infected with NSI forms of HIV-1, comprising:
    (a) obtaining CCR5 transcript RNA of said individual, wherein said CCR5 transcript RNA is obtained from whole blood or peripheral blood mononuclear cells of the individual;
    (b) amplifying said CCR5 transcript RNA by using a transcription based amplification using a pair of oligonucleotides that target sequences of CCR5 gene spanning positions 450 through 650;
    (c) determining whether an amplification product of step (a) contains a wild type CCR5 allele, a mutant CCR5 allele or both wild type and mutant CCR5 alleles by independently hybridizing amplification product with labelled wild type and mutant specific probes and detecting the resulting hybridization products, and
    (d) predicting susceptibility of said individual to infection by NSI forms of HIV-1 and predicting disease progression depending on whether said individual is homozygous wild type, heterozygous or homozygous mutant for the CCR5 alleles.

12. A test kit for the diagnosis of infectability of individuals to NSI forms of HIV-1 comprising:
    (a) a pair of oligonucleotides for amplifying CCR5 RNA transcript by a transcription based amplification method,
    (b) an oligonucleotide DNA probe for detecting a wild type CCR5 allele, and
    (c) an oligonucleotide DNA probe for detecting a mutant CR5 allele.

13. The kit of claim 12, further comprising a capture probe for liquid hybridization based ECL (electrochemiluminescence) analysis.

14. The kit of claim 12, wherein one of said pair of oligonucleotides is selected from two antisense P1 sequences having map positions 602 to 623 and 620 to 650 of the CCR5 gene and the other oligonucleotide is selected from two P2 sequences having map positions 465 to 486 and 430 to 454 of the CCR5 gene.

15. The kit of claim 14, wherein the P1 and P2 sequences are:

P 1 A =
5'AATTCTAATACGACTCACTATAGGGAGCAGC GGCAGGACCAGCCCCA3'[SEQ ID NO:1];

P 1 B =
5'AATTCTAATACGACTCACTATAGG-GAGAGATTCCCGAGTAGCAGATGA CCATGA3' [SEQ ID NO:2];

P2A=5'GGCTGTGTTTGCGTCTCTCCCA3'[SEQ ID NO:3]; and

P2B=5'TTTGGGGTGGTGACAAGTGTGATCA3'[SEQ ID NO:6], where the italicized sequence designates T7 promoter sequence.

16. The kit of claim 12, wherein said wild type probe has the sequence:

5'AGTATCAATTCTGGAAGAATTTCCA3'[SEQ ID NO:7];

and said mutant probe has the sequence:

5'TCATTTTCCATACATTAAAGATAGTCAT3'[SEQ ID NO:8].

17. The kit of claim 13, wherein said wild type probe has the sequence:

5'AGTATCAATTCTGGAAGAATTTCCA3'[SEQ ID NO:7], said mutant probe has the sequence:

5'TCCATACATTAAAGAT3'[SEQ ID NO:9], and said capture probe has the sequence:

bio-5'AAAGAAGGTCTTCATTACACCTGCAGC3' [SEQ ID NO:10].

18. The kit of claim 12, further comprising reagents for transcription based amplification of CCR5 RNA transcript.

* * * * *